US012620493B2

(12) United States Patent
Sinha et al.

(10) Patent No.: US 12,620,493 B2
(45) Date of Patent: May 5, 2026

(54) THROMBUS TREATMENT METRIC

(71) Applicant: KONINKLIJKE PHILIPS N.V.,
Eindhoven (NL)

(72) Inventors: Ayushi Sinha, Baltimore, MD (US);
Javad Fotouhi, Cambridge, MA (US);
Vipul Shrihari Pai Raikar, Somerville,
MA (US); Leili Salehi, Waltham, MA
(US); Ramon Quido Erkamp,
Swampscott, MA (US); Sean Kyne,
Brookline, MA (US)

(73) Assignee: Koninklijke Philips N.V., Eindhoven
(NL)

( * ) Notice: Subject to any disclaimer, the term of this
patent is extended or adjusted under 35
U.S.C. 154(b) by 382 days.

(21) Appl. No.: 18/074,738

(22) Filed: Dec. 5, 2022

(65) Prior Publication Data

US 2023/0178248 A1 Jun. 8, 2023

Related U.S. Application Data

(60) Provisional application No. 63/287,165, filed on Dec.
8, 2021.

(30) Foreign Application Priority Data

Feb. 14, 2022 (EP) .................................... 22156482

(51) Int. Cl.
*G16H 50/30* (2018.01)
*A61B 6/50* (2024.01)
(Continued)

(52) U.S. Cl.
CPC ............. *G16H 50/30* (2018.01); *A61B 6/504*
(2013.01); *G16H 20/30* (2018.01); *G16H*
*30/40* (2018.01); *G16H 50/20* (2018.01)

(58) Field of Classification Search
CPC ........ G16H 50/30; G16H 20/30; G16H 30/40;
G16H 50/20; A61B 6/504
See application file for complete search history.

(56) References Cited

U.S. PATENT DOCUMENTS 10,898,152 B1 1/2021 Kim et al.
11,147,635 B1 * 10/2021 Sganga .................. G16H 20/40
(Continued)

FOREIGN PATENT DOCUMENTS

WO 2018137949 A1 8/2018
WO 2021188843 A1 9/2021

OTHER PUBLICATIONS

Alverne, F., Lima, F. O., Rocha, et al. Unfavorable Vascular
Anatomy during Endovascular Treatment of Stroke: Challenges and
Bailout Strategies. Journal of stroke 22(2): 185-202 (2020). https://
doi.org/10.5853/jos.2020.00227.
(Continued)

*Primary Examiner* — Eliza A Lam

(57) ABSTRACT
A computer-implemented method of predicting a success
metric, achieved by performing a treatment procedure on a
thrombus, is provided. The method includes: receiving
angiographic image data, including one or more angio-
graphic images comprising the thrombus; inputting the
angiographic image data into a model, comprising a neural
network, configured to output a prediction related to the
treatment procedure; and calculating the success metric
based on the output of the model.

14 Claims, 5 Drawing Sheets

(51) Int. Cl.

| | |
|---|---|
| *G16H 20/30* | (2018.01) |
| *G16H 30/40* | (2018.01) |
| *G16H 50/20* | (2018.01) |

(56) References Cited

U.S. PATENT DOCUMENTS

| | | | | |
|---|---|---|---|---|
| 11,622,713 | B2 * | 4/2023 | Ben-Haim | .......... A61B 5/0538 |
| | | | | 606/34 |
| 2016/0180042 | A1 * | 6/2016 | Menon | ................ A61B 5/0042 |
| | | | | 705/2 |
| 2020/0120233 | A1 | 4/2020 | Annunziata et al. | |
| 2020/0184660 | A1 | 6/2020 | Shi et al. | |
| 2021/0007760 | A1 * | 1/2021 | Reisin | ................... G16H 40/63 |
| 2021/0137384 | A1 * | 5/2021 | Robinson | .................. G06T 7/10 |
| 2021/0236080 | A1 | 8/2021 | Herrmann et al. | |
| 2021/0334935 | A1 | 10/2021 | Grigoriev et al. | |
| 2021/0334965 | A1 | 10/2021 | Min et al. | |
| 2021/0343063 | A1 | 11/2021 | Garbin et al. | |
| 2023/0083484 | A1 * | 3/2023 | Milner | ................ A61B 5/0066 |
| | | | | 600/301 |

OTHER PUBLICATIONS

Bernava G, Rosi A, Boto J, et al. Direct thromboaspiration efficacy for mechanical thrombectomy is related to the angle of interaction between the aspiration catheter and the clot. Journal of NeuroInterventional Surgery 12(4): 396-400 (2020).

Ramalho, T. et al., entitled "Density estimation in representation space to predict model uncertainty", https://arxiv.org/pdf/1908.07235.pdf.

Figure 7(c) from Constantinou I, Jendrusch M, Aspert T, et al. Self-Learning Microfluidic Platform for Single-Cell Imaging and Classification in Flow. Micromachines 10(5): 311 (2019). https://doi.org/10.3390/mi10050311.

\* cited by examiner

THROMBUS TREATMENT METRIC

CROSS REFERENCE TO RELATED APPLICATIONS

This application claims the benefit of U.S. Provisional Patent Application No. 63/287,165 filed Dec. 8, 2021 and European Patent Application Number 22156482.6 filed Feb. 14, 2022. These applications are hereby incorporated by reference herein.

TECHNICAL FIELD

The present disclosure relates to predicting a success metric that will be achieved by performing a treatment procedure on a thrombus. A computer-implemented method, a computer program product, and a system, are disclosed.

BACKGROUND

A thrombus, or clot, is a blockage in a blood vessel. A thrombus may occur in a vein or in an artery. In the former case, i.e. a venous thrombus, blood becomes congested, leading to swelling and fluid congestion. In the latter case, i.e. an arterial thrombus, the supply of blood is restricted, leading to a condition known as ischemia, which risks damage to tissue supplied by the artery. In both cases, a portion of the thrombus can also break-away as an embolus. The embolus can become lodged elsewhere in the body and form an embolism that likewise blocks a blood vessel. Thromboses may occur in various parts of the body, including in the heart and the brain, where their effects can be severe unless treated quickly. In the brain, for example, a thrombus, or an embolism, can lead to conditions such as (ischemic) stroke.

Various treatments are available for treating thromboses. These include pharmacological treatments in which thrombolytic drugs such as Alteplase are administered in order to break-up a thrombus by means of thrombolysis. Various treatment procedures are also available for treating thromboses. Such treatment procedures include the use of treatment devices such as mechanical thrombectomy devices, and which are used in so-called mechanical thrombectomy procedures.

At present, there are two main groups of mechanical thrombectomy devices: aspiration catheters, and stent retrievers. Aspiration catheters typically include a delivery catheter that is used to deliver an irrigation fluid to the thrombus, and an extraction catheter that is used to extract the irrigation fluid, together with broken-up pieces of the thrombus. In-use, an aspiration catheter is positioned close to the clot, and at which position the aspiration takes place, resulting in the broken pieces of the clot being extracted from the body. Stent retrievers typically include an expandable wire mesh tube that is designed to remove the clot in one piece. In-use, a stent retriever is positioned close to the thrombus using a delivery catheter. After positioning the delivery catheter, the wire mesh tube is extended out of the delivery catheter, where it expands and captures the clot. The stent retriever is then withdrawn into the delivery catheter and the stent retriever, together with the clot, is removed from the body.

In some studies, mechanical thrombectomy devices have been shown to have a higher clinical efficacy in achieving re-perfusion of blood vessels than thrombolytic drugs. The success of mechanical thrombectomy procedures in reducing long-term functional dependency and mortality has been found to be highly correlated with the "technical success" of the procedure. Technical success is assessed based on several criteria, including the speed of the procedure and completeness of re-perfusion. That is, if complete re-perfusion is achieved but only after a lengthy procedure, or if the procedure is fast but complete re-perfusion is not achieved, then a patient is likely to have poor long-term outcome. Achieving complete re-perfusion in the first pass has been shown to have a strong correlation with positive long-term outcome in patients. However, a physician typically takes several attempts to successfully remove a thrombus.

Recent publications have shown that the location of the thrombus with respect to the anatomy can affect the success of different types of mechanical thrombectomy procedures. This is described in a document by Alverne, F., et al., entitled "Unfavorable Vascular Anatomy during Endovascular Treatment of Stroke: Challenges and Bailout Strategies", Journal of stroke 22(2): 185-202 (2020), and in another document by Bernava, G., et al., entitled "Direct thromboaspiration efficacy for mechanical thrombectomy is related to the angle of interaction between the aspiration catheter and the clot", Journal of NeuroInterventional Surgery 12(4): 396-400 (2020).

As mentioned in these two documents, the tortuosity of a vessel in the vicinity of the thrombus can indicate the likely success of a mechanical thrombectomy procedure. When unfavorable vascular anatomy, such as tortuosity, is combined with sub-optimal device selection and/or placement, this can result in a poor long-term outcome for a patient. The location of a thrombus within tortuous intracerebral arteries can for example affect the success of both stent retriever and aspiration catheter based treatments, as described in the aforementioned document by Alverne, F., et al. If the location of the thrombus allows the force applied to a stent retriever during its withdrawal into the delivery catheter to be in the same direction, or in a similar direction, throughout the withdrawal, then the chance of successfully retrieving the thrombus is high. However, if the direction of the force applied to the stent retriever changes significantly during its withdrawal into the delivery catheter, for example due to the tortuosity of the vasculature, then the probability of successful retrieval are low. Therefore, changes in the angle of the force applied to the stent retriever during the withdrawal of the thrombus into the delivery catheter affect the success of stent retriever-based treatments. Similarly, for aspiration catheter-based treatments, an angle of interaction between the aspiration catheter and the thrombus of >125.5 degrees, has been associated with high chance of success, as described in the aforementioned document by Bernava, G., et al. In this document, an angle of interaction of 180 degrees occurs when a distal end of the aspiration catheter and the thrombus lie in a straight line.

Owing to the multitude of factors that can affect the success of a thrombus treatment procedures, it is challenging to determine the success that may be achieved by an approach. Consequently, there is a need for an improved approach to predicting the success that will be achieved by a treatment procedure on a thrombus.

SUMMARY

According to one aspect of the present disclosure, a computer-implemented method of predicting a success metric for a treatment procedure performable on a thrombus. The method includes:

- receiving current angiographic image data that includes an angiographic image comprising the thrombus;

inputting the angiographic image into a model configured to output a prediction, related to performance of the treatment procedure, based on the angiographic image; and calculating the success metric for the treatment procedure based on the output of the model.

According to another aspect of the present disclosure, a system for predicting a success metric for a treatment procedure performable on a thrombus. The system includes:

an imaging system configured to generate current angiographic image data including one or more angiographic images comprising the thrombus; and a controller configured to:

receive current angiographic image data that includes an angiographic image comprising the thrombus;

input the angiographic image into a model configured to output a prediction, related to performance of the treatment procedure, based on the angiographic image; and calculate the success metric for the treatment procedure based on the output of the model.

According to another aspect of the present disclosure, a non-transitory computer-readable storage medium having stored a computer program comprising instructions for predicting a success metric for a treatment procedure performable on a thrombus, the instructions, when executed by a processor, cause the processor to:

receive current angiographic image data that includes an angiographic image comprising the thrombus;

input the angiographic image into a model configured to output a prediction, related to performance of the treatment procedure, based on the angiographic image; and calculate the success metric for the treatment procedure based on the output of the model.

In some embodiments of the method, system, and non-transitory computer-readable storage medium, the model comprises a neural network. In some embodiments, the non-transitory computer-readable storage medium further includes training of the model, to output the prediction related to the treatment procedure, based on training data comprising angiographic training images representing the treatment procedure and corresponding ground truth outcome data of the treatment procedure.

The result of these operations is to provide a reliable success metric indicating the success that may be achieved by the treatment procedure. Since the success metric is based on the angiographic images of a patient, it may account for factors such as the tortuosity of the vasculature in the vicinity of the thrombus.

Further aspects, features, and advantages of the present disclosure will become apparent from the following description of examples, which is made with reference to the accompanying drawings.

DETAILED DESCRIPTION

Figure 1:
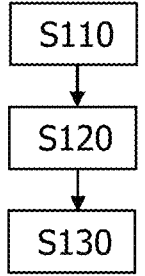
FIG. 1 is a flowchart illustrating an example of a method of predicting a success metric achieved by performing a treatment procedure on a thrombus, in accordance with some aspects of the present disclosure.

Examples of the present disclosure are provided with reference to the following description and figures. In this description, for the purposes of explanation, numerous specific details of certain examples are set forth. Reference in the specification to "an example", "an implementation" or similar language means that a feature, structure, or characteristic described in connection with the example is included in at least that one example. It is also to be appreciated that features described in relation to one example may also be used in another example, and that all features are not necessarily duplicated in each example for the sake of brevity. For instance, features described in relation to a computer implemented method, may be implemented in a computer program product, and in a system, in a corresponding manner.

In the following description, reference is made to computer-implemented methods and systems that involve predicting a success metric achieved by performing a treatment procedure on a thrombus. It is to be appreciated that the success metric may be predicted prior to, or during a treatment procedure. In other words, the success metric may be predicted for a planned treatment procedure, or alternatively it may be predicted for a current treatment procedure. Reference is made to examples in which the thrombus is located in a blood vessel. In general, the thrombus may be located in a vein, or in an artery. In other words, the thrombus may be a venous thrombus, or alternatively it may be an arterial thrombus. It is to be appreciated that the thrombus may be located in various parts of the body, including in the brain, the heart, the lungs, or in a limb such as the leg, for example. In some examples the thrombus may be located in the brain and, the purpose of the treatment procedure may be for the treatment of (ischemic) stroke.

Reference is also made herein to examples in which the treatment procedure is a mechanical thrombectomy procedure. At present, there are two main groups of mechanical thrombectomy devices that are used in such procedures: aspiration catheters, and stent retrievers. Examples are described herein wherein the mechanical thrombectomy device is one of these two types of device. However, it is to be appreciated that the computer-implemented methods and systems described herein may also be used with other types of mechanical thrombectomy devices, for example, coil retrievers. Moreover, it is to be appreciated that the methods described herein may be used to predict a success metric achieved with other types of treatment procedures and in which other types of devices are used to treat a thrombus. These include ultrasound thrombolysis devices, for example, and wherein ultrasound energy is used to break-up a thrombus, and also rheolytic or rotational embolectomy devices wherein pressurized saline or a rotating device, respectively, are used to macerate or fragment the thrombus which is then aspirated by an aspiration catheter.

Reference is also made herein to examples of a model that comprises a neural network. However, it is to be appreciated that the computer-implemented methods and systems described herein may be implement with other types of machine learning frameworks, algorithms, etc. without limitation.

It is noted that the computer-implemented methods disclosed herein may be provided as a non-transitory computer-readable storage medium including computer-readable instructions stored thereon, which, when executed by at least one processor, cause the at least one processor to perform the method. In other words, the computer-implemented methods may be implemented in a computer program product or as a controller. The computer program product or controller can be provided by dedicated hardware, or hardware capable of running the software in association with appropriate software. When provided by a processor, the functions of the method features can be provided by a single dedicated processor, or by a single shared processor, or by a plurality of individual processors, some of which can be shared. The functions of one or more of the method features may for instance be provided by processors that are shared within a networked processing architecture such as a client/server architecture, a peer-to-peer architecture, the Internet, or the Cloud.

The explicit use of the terms "processor" or "controller" should not be interpreted as exclusively referring to hardware capable of running software, and can implicitly include, but is not limited to, digital signal processor "DSP" hardware, read only memory "ROM" for storing software, random access memory "RAM", a non-volatile storage device, and the like. Furthermore, examples of the present disclosure can take the form of a computer program product accessible from a computer-usable storage medium, or a computer-readable storage medium, the computer program product providing program code for use by or in connection with a computer or any instruction execution system. For the purposes of this description, a computer-usable storage medium or a computer readable storage medium can be any apparatus that can comprise, store, communicate, propagate, or transport a program for use by or in connection with an instruction execution system, apparatus, or device. The medium can be an electronic, magnetic, optical, electromagnetic, infrared, or a semiconductor system or device or propagation medium. Examples of computer-readable media include semiconductor or solid state memories, magnetic tape, removable computer disks, random access memory "RAM", read-only memory "ROM", rigid magnetic disks and optical disks. Current examples of optical disks include compact disk-read only memory "CD-ROM", compact disk-read/write "CD-R/W", Blu-Ray™ and DVD.

As mentioned above, it can be challenging to determine the success that may be achieved by a thrombus treatment procedure. Currently, a physician may make an intuitive decision as to which of multiple treatment procedures to use. However, owing to the multitude of factors that can affect the success of a thrombus treatment procedure, this may lead to the selection of a procedure that is sub-optimal.

FIG. 1 is a flowchart illustrating an example of a method of predicting a success metric achieved by performing a treatment procedure on a thrombus, in accordance with some aspects of the present disclosure. With reference to FIG. 1, the method includes:

receiving S110 angiographic image data, including one or more angiographic images 130 comprising the thrombus 120;

inputting S120 the angiographic image data into a model which comprises a neural network 140 or other machine learning framework; and calculating S130 the success metric 110 based on the output of the model comprising the neural network 140; and wherein the model comprising the neural network 140 is trained using training data comprising angiographic training images 130' representing the treatment procedure, and corresponding ground truth procedure outcome data.

The result of these operations is to provide a reliable success metric indicating the success that may be achieved by the treatment procedure. Since the success metric is based on the angiographic images of a patient, it may account for factors such as the tortuosity of the vasculature in the vicinity of the thrombus.

Figure 2:
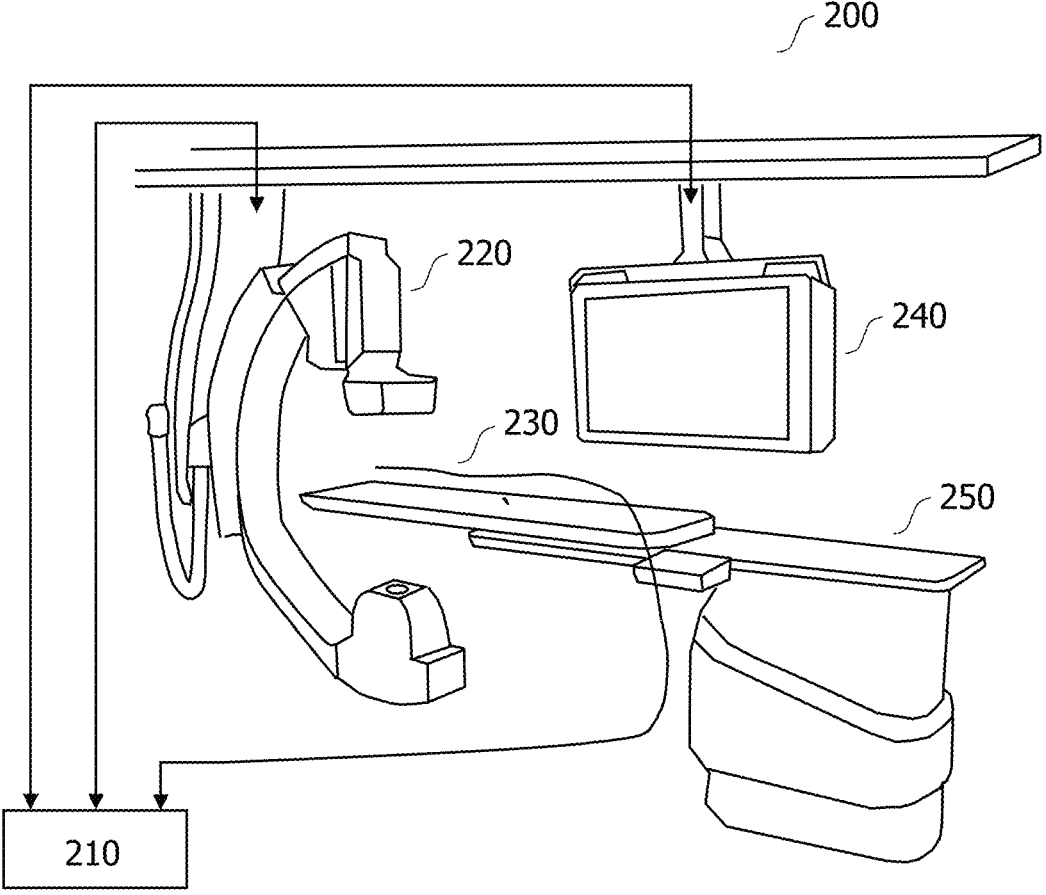
FIG. 2 is a schematic diagram illustrating an example of a system 200 for predicting a success metric achieved by performing a treatment procedure on a thrombus, in accordance with some aspects of the present disclosure.

The method described above may also be implemented by the system illustrated in FIG. 2, which is a schematic diagram illustrating an example of a system 200 for predicting a success metric achieved by performing a treatment procedure on a thrombus, in accordance with some aspects of the present disclosure. Thus, operations described in relation to the flowchart illustrated in FIG. 1, may also be performed by the system 200 illustrated in FIG. 2, and vice versa.

With reference to FIG. 1, in the operation S110, angiographic image data, including one or more angiographic images 130 comprising the thrombus 120, is received. In general, the angiographic image data may include one or more 2D angiographic images, i.e. angiographic "projection" images. Alternatively, the angiographic image data may include one or more 3D angiographic images, i.e. angiographic "volumetric" images.

In general, the 2D angiographic images may be generated by a projection X-ray imaging system. Projection X-ray imaging systems typically include a support arm such as a so-called "C-arm", or an "O-arm", that supports an X-ray source-detector arrangement. Projection X-ray imaging systems may alternatively include a support arm with a different shape to these examples. Projection X-ray imaging systems typically generate projection X-ray images with the support arm held in a static position with respect to an imaging region during the acquisition of image data. In some examples, the 2D angiographic images 130 may be fluoroscopic, i.e. live images. In some examples, the 2D angiographic images 130 may be generated using a digital subtraction angiography "DSA" technique, and wherein each image is generated by subtracting from the image the corresponding pixel intensities of a background image. The 2D angiographic images may be generated by the projection X-ray imaging system 220 illustrated in FIG. 2, for example By way of an example, the 2D angiographic images may be generated by the Philips Azurion 7 X-ray imaging system marketed by Philips Healthcare, Best, The Netherlands.

In general, the 3D angiographic images may be generated by a volumetric imaging system, such as for example a volumetric X-ray imaging system. A volumetric X-ray imaging system typically generates image data whilst rotating, or stepping, an X-ray source-detector arrangement around an imaging region, and subsequently reconstructs the image data obtained from multiple rotational angles into a 3D, or volumetric image. Examples of volumetric X-ray imaging systems include computed tomography "CT" imaging systems, cone beam CT "CBCT" imaging systems, and spectral CT imaging systems. Examples of 3D angiographic images include CT angiography "CTA" and 3D rotational angiography "3DRA" images. In some examples, the 3D angiographic images 130 may be fluoroscopic, i.e. live images. In some examples, the 3D angiographic images 130 may be generated using a digital subtraction angiography "DSA" technique. Alternatively, the 3D angiographic images may be generated by a magnetic resonance imaging "MRI" system. For example, magnetic resonance angiography "MRA" volumetric image data may be generated by injecting a contrast agent into the vasculature and using oscillating magnetic fields at specific resonance frequencies to generate images of various anatomical structures using an MRI imaging system.

In some examples, a single image is received in the operation S110, whereas in other examples, multiple images are received in the operation S110. The multiple images may form a temporal sequence of images, wherein the images are generated at regular time intervals. Alternatively, the multiple images may be generated intermittently, i.e. on an ad-hoc basis.

The angiographic image data received in the operation S110 may be received from an imaging system, such as one of the imaging systems described above, or from a computer readable storage medium, or from the Internet or the Cloud, for example. The angiographic image data may be received by the one or more processors 210 illustrated in FIG. 2. The angiographic image data may be received via any form of data communication, including wired, optical, and wireless communication. By way of some examples, when wired or optical communication is used, the communication may take place via signals transmitted on an electrical or optical cable, and when wireless communication is used, the communication may for example be via RF or optical signals.

In the operation S120, the angiographic image data is inputted into a model that comprises a neural network 140. The neural network 140 of the model is trained using training data comprising angiographic training images 130' representing the treatment procedure, and corresponding ground truth procedure outcome data. The angiographic training images 130' represent the treatment procedure on a thrombus. The treatment procedure may for example be a mechanical thrombectomy procedure. The mechanical thrombectomy procedure may be performed using a stent retriever device, or a catheter aspiration device, for example. The angiographic training images 130' may be 2D or 3D angiographic images, as described above for the images that are inputted into the neural network of the model in the operation S120.

In general, the ground truth procedure outcome data that corresponds to the angiographic training images 130' may include one or more outcome factors. The outcome factors may include a classified outcome, such as a success or a failure of the procedure. The classified outcome may include an associated probability of its occurrence. For example, the success of the procedure may include a percentage probability of success. Alternatively or additionally, the ground truth procedure outcome data may include outcome factors such as a speed of the procedure, a measure of completeness of re-perfusion being achieved by the procedure, a 90-day mortality, or a 90-day modified Rankin Scale (mRS), and whether the procedure needed to be repeated. Such outcome factors may likewise include an associated probability of their occurrence.

In the operation S130, a success metric 110 is calculated based on the output of the neural network 140 of the model. In this operation, the calculated success metric 110 may for example be a success or failure of the procedure. The success metric may include an associated probability of its occurrence. Various techniques for calculating the success metric are described in the examples below. In general, these include directly predicting the success metric using the neural network, and analyzing the ground truth procedure outcome data for the angiographic training images 130 in order to provide the success metric 110. As described in the examples below, in the former case, the ground truth procedure outcome data that is used to train the neural network includes one or more outcome factors that represent the success metric 110, and at inference the neural network predicts an expected outcome that similarly includes one or more outcome factors. At inference, the one or more outcome factors of the expected outcome that is predicted by the neural network, are used to calculate the success metric. In the latter case, the ground truth procedure outcome data that is used to train the neural network includes one or more outcome factors representing the success metric, and at inference, the one or more outcome factors of some of the ground truth procedure outcome data, specifically the one or more outcome factors of ground truth procedure outcome data of angiographic training images having latent space representations within a predetermined distance of the latent space representation of the inputted angiographic image, are analysed to provide the success metric 110. The success metric 110 is then outputted, and may thus be used to inform a user on the suitability of a particular treatment procedure for treating the thrombus. The success metric may be outputted to a display, such as the display 240 illustrated in FIG. 2, for example.

Various examples of the neural network 140 and its training are described in detail below. In general, the neural network 140 may include one or more architectures, such as for example a convolutional neural network "CNN", an autoencoder network, or one its variants (e.g., variational autoencoder "VAE", maximum mean discrepancy "MMD" VAE, etc.). The encoder and decoder components of the autoencoder may include a convolutional neural network "CNN" architecture, or a recurrent neural network "RNN" or transformer architecture.

In general, the training of a neural network involves inputting a training dataset into the neural network, and iteratively adjusting the neural network's parameters until the trained neural network provides an accurate output. Training is often performed using a Graphics Processing Unit "GPU" or a dedicated neural processor such as a Neural Processing Unit "NPU" or a Tensor Processing Unit "TPU". Training often employs a centralized approach wherein cloud-based or mainframe-based neural processors are used to train a neural network. Following its training with the training dataset, the trained neural network may be deployed to a device for analyzing new input data during inference. The processing requirements during inference are significantly less than those required during training, allowing the neural network to be deployed to a variety of systems such as laptop computers, tablets, mobile phones and so forth. Inference may for example be performed by a Central Processing Unit "CPU", a GPU, an NPU, a TPU, on a server, or in the cloud.

The process of training the neural network 140 described above therefore includes adjusting its parameters. The parameters, or more particularly the weights and biases, control the operation of activation functions in the neural network. In supervised learning, the training process automatically adjusts the weights and the biases, such that when presented with the input data, the neural network accurately provides the corresponding expected output data. In order to do this, the value of the loss functions, or errors, are computed based on a difference between predicted output data and the expected output data. The value of the loss function may be computed using functions such as the negative log-likelihood loss, the mean absolute error (or L1 norm), the mean squared error, the root mean squared error (or L2 norm), the Huber loss, or the (binary) cross entropy loss. During training, the value of the loss function is typically minimized, and training is terminated when the value of the loss function satisfies a stopping criterion. Sometimes, training is terminated when the value of the loss function satisfies one or more of multiple criteria.

Various methods are known for solving the loss minimization problem such as gradient descent, Quasi-Newton methods, and so forth. Various algorithms have been developed to implement these methods and their variants including but not limited to Stochastic Gradient Descent "SGD", batch gradient descent, mini-batch gradient descent, Gauss-Newton, Levenberg Marquardt, Momentum, Adam, Nadam, Adagrad, Adadelta, RMSProp, and Adamax "optimizers" These algorithms compute the derivative of the loss function with respect to the model parameters using the chain rule. This process is called backpropagation since derivatives are computed starting at the last layer or output layer, moving toward the first layer or input layer. These derivatives inform the algorithm how the model parameters must be adjusted in order to minimize the error function. That is, adjustments to model parameters are made starting from the output layer and working backwards in the network until the input layer is reached. In a first training iteration, the initial weights and biases are often randomized. The neural network then predicts the output data, which is likewise, random. Backpropagation is then used to adjust the weights and the biases. The training process is performed iteratively by making adjustments to the weights and biases in each iteration. Training is terminated when the error, or difference between the predicted output data and the expected output data, is within an acceptable range for the training data, or for some validation data. Subsequently the neural network may be deployed, and the trained neural network makes predictions on new input data using the trained values of its parameters. If the training process was successful, the trained neural network accurately predicts the expected output data from the new input data.

Returning to the flowchart in FIG. 1, a confidence value may also be calculated for each of the angiographic images 130 that are inputted into the trained neural network 140 in the operation S120. The confidence values may then be outputted. The confidence values may be outputted to a display, such as the display illustrated in FIG. 2, for example. The confidence values represent a confidence of the predictions made by the neural network 140, and permit decisions to be made based on the success metric. For example, if the confidence is low, it might be decided not to rely upon the success metric 110. In this regard, a warning may be outputted if the confidence value is below a predetermined threshold value.

An example of a technique for generating confidence values associated with a neural network's predictions is disclosed in a document by Ramalho, T. et al., entitled "Density estimation in representation space to predict model uncertainty", https://arxiv.org/pdf/1908.07235.pdf. The neural network 140 may be trained in accordance with this technique to generate confidence values such that when the neural network 140 is presented with an image that is significantly different from its training dataset, the neural network 140 it is able to recognize this and the neural network 140 outputs a low confidence value. The technique described in this document generates confidence values by estimating the training data density in representation space, and determining whether the trained network is expected to make a correct prediction for the input by measuring the distance in representation space between the input and its closest neighbors in the training set. Alternative techniques may also be used to generate confidence values associated with the predictions of the neural network 140. For instance, in some examples described below, the neural network is trained to reconstruct the angiographic images that are inputted into the neural network. In these examples, a confidence value may be calculated based on a difference, i.e. error, between the reconstructed angiographic image and the inputted angiographic image. If the error is small, the confidence value may be high, whereas if the error is large, the confidence value may be lower. Alternatively, the dropout technique may be used to generate confidence values for the angiographic images 130 that are inputted into the trained neural network 140. The dropout technique involves iteratively inputting the same data into a neural network and determining the neural network's output whilst randomly excluding a proportion of the neurons from the neural network in each iteration. The outputs of the neural network are then analyzed to provide mean and variance values. The mean value represents the final output, and the magnitude of the variance indicates whether the neural network is consistent in its predictions, in which case the variance is small and confidence high, or whether the neural network was inconsistent in its predictions, in which case the variance is larger and confidence low.

Various examples of the neural network 140, and its training, are now described.

In one example, the neural network 140 is trained to generate latent space representations $z_i$ representing the inputted angiographic images 130, and at inference, the success metric 110 is calculated by analyzing the ground truth procedure outcome data $150'_{GT}$ of angiographic training images 130' having similar latent space representations $z_t$ to the inputted angiographic images 130. This example is described with reference to FIG. 3, which is a schematic diagram illustrating A) a first example of the training of a neural network 140 to generate latent space representations $z_t$ of inputted angiographic images 130', and B) the performance of inference with the trained first example of a neural network 140, in accordance with some aspects of the present disclosure.

Figure 3:
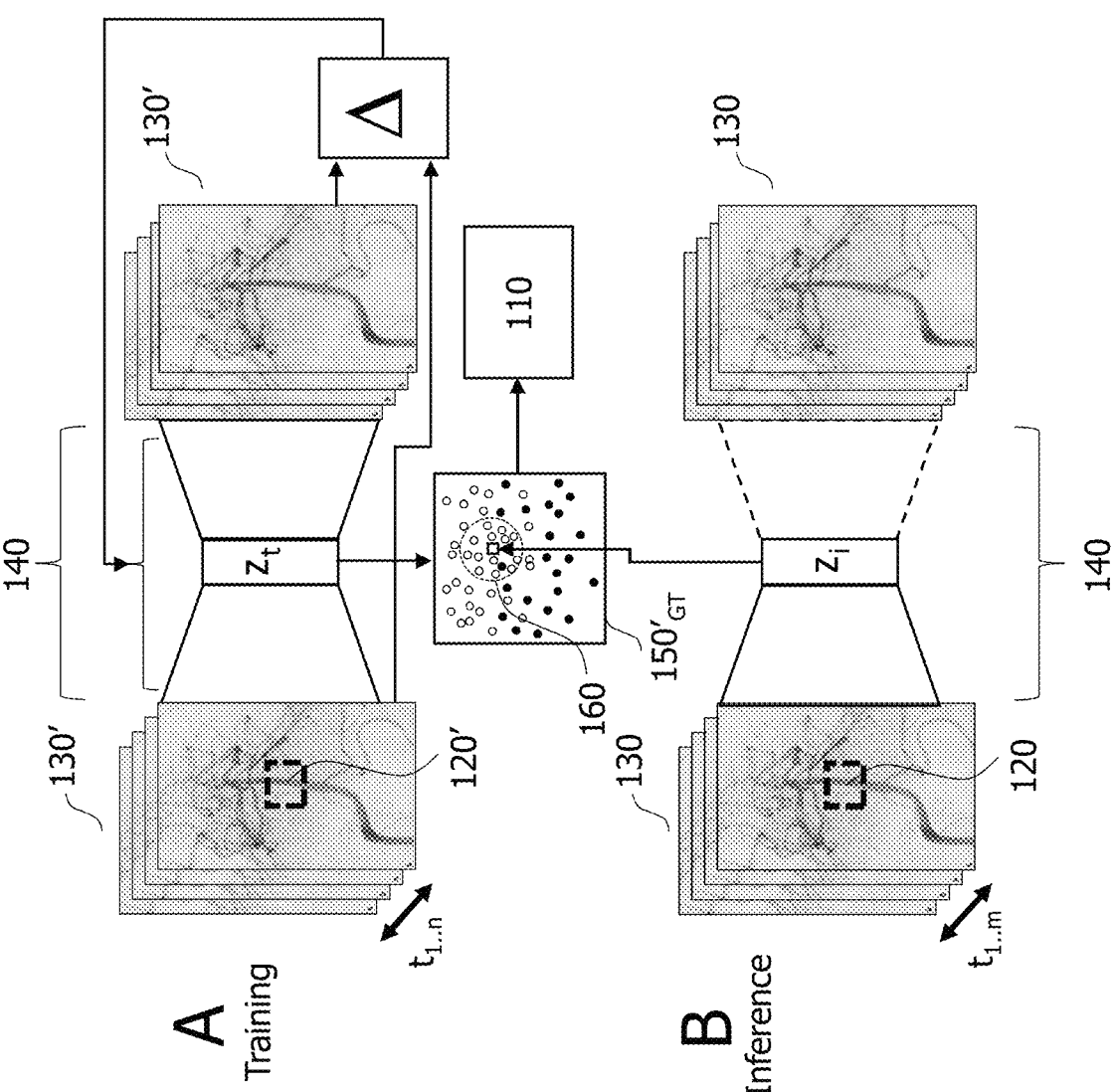
FIG. 3 is a schematic diagram illustrating A) a first example of the training of a neural network 140 to generate latent space representations $z_t$ of inputted angiographic images 130', and B) the performance of inference with the trained first example of a neural network 140, in accordance with some aspects of the present disclosure.

As illustrated in FIG. 3, in this example, the neural network 140 may be provided by an autoencoder, or one of its variants (e.g., variational autoencoder "VAE", maximum mean discrepancy "MMD" VAE, etc.). Starting with the training of the neural network, and with reference to FIG. 3A, in this example, the neural network 140 is trained by forcing the neural network 140 reconstruct the angiographic training images 130' that are inputted into the neural network. With reference to FIG. 3A, the encoder component of the autoencoder on the left-hand side of the neural network 140 compresses each of the inputted angiographic training images 130', into a reduced dimension latent representation $z_t$. The decoder component of the autoencoder on the right-hand side of the neural network 140 decodes, or reconstructs, each inputted angiographic training image 130' from the latent representation $z_t$. During training, the goal is to learn a reduced dimension embedding space, and in which distances between embeddings are indicative of a similarity between the inputted angiographic training images. The encoder and decoder components of the autoencoder may be provided by a convolutional neural network "CNN" architecture when the input into the neural network is a single image, or by a recurrent neural network "RNN" or transformer architecture when the input to the neural network includes multiple images, such as a temporal sequence of images.

In this example, the neural network 140 is trained to generate latent space representations $z_i$ representing the inputted angiographic images 130, by:

receiving angiographic training data, including a plurality of angiographic training images 130', and wherein each training image comprises a thrombus 120';

inputting the angiographic training data into the neural network 140; and for each of a plurality of the inputted angiographic training images 130':

generating a latent space representation $z_t$ of the inputted angiographic training image, using the neural network 140;

reconstructing the inputted angiographic training image 130' from the latent space representation $z_t$, using the neural network 140; and adjusting parameters of the neural network 140 based on a difference between the inputted angiographic training image and the reconstructed inputted angiographic training image; and repeating the generating, the reconstructing, and the adjusting, until a stopping criterion is met.

In this example, the angiographic training data that is used to train the neural network 140 may include 2D or 3D angiographic training images 130', as described above for the images that are inputted into the neural network in the operation S120. The adjusting of the parameters of the neural network 140 during training may be performed using backpropagation, as described above. The difference between the inputted angiographic training image and the reconstructed inputted angiographic training image, and which is used to adjust the parameters of the neural network 140, is illustrated in FIG. 3 by the symbol D. As mentioned above, the value of this difference may be calculated using a loss function such as L1 norm, L2 norm, binary cross entropy, and so forth.

The result of the training operation is that the neural network 140 is trained to provide the latent space representations $z_t$ for the training images, and from which the original training images can be accurately reconstructed. At inference, the latent space representations $z_t$ of the training images are used, together with their corresponding ground truth procedure outcome data 150'$_{GT}$, to calculate the success metric 110 for new inputted angiographic images 130.

In this example, the neural network 140 is thus trained to generate latent space representations $z_i$ representing the inputted angiographic images 130. During inference, the method described with reference to FIG. 1 includes:

generating, for each inputted angiographic image, a latent space representation $z_i$, using the neural network 140; and wherein the calculating S130 the success metric 110 based on the output of the neural network 140, comprises analyzing the ground truth procedure outcome data 150'$_{GT}$ of angiographic training images 130' having latent space representations $z_t$ within a predetermined distance 160 of the latent space representation $z_i$ of the inputted angiographic image, and calculating the success metric 110 for the inputted angiographic image based on the analyzed ground truth procedure outcome data.

With reference to FIG. 3B, at inference, the trained neural network 140 generates a latent space representation $z_i$ for each inputted angiographic image 130 (when using a CNN based implementation) or for a set of inputted angiographic images (when using an RNN based implementation). The trained encoder component of the VAE neural network 140 on the left-hand side of FIG. 3B is used for this purpose. It is noted that the trained decoder component of the VAE neural network 140 on the right-hand side of FIG. 3B is not essential for inference, although it may be used to calculate confidence values, as described below. The ground truth procedure outcome data 150'$_{GT}$ of angiographic training images 130' having similar latent space representations $z_t$ to the latent space representation $z_i$ of the inputted angiographic image, are then analyzed in order to calculate the success metric for the inputted image. The latent space representations $z_t$ of the angiographic training images 130' are illustrated by the circular symbols in the central portion of FIG. 3. The corresponding ground truth procedure outcome data 150' GT for each latent space representation $z_t$ is illustrated by an un-filled circular symbol for a successful procedure, and by a dark-filled circular symbol for an unsuccessful procedure. The latent space representation $z_i$ of an inputted angiographic image 130 that is inputted during inference, is illustrated by the square symbol amongst the circular symbols of the training angiographic images. The relative positions of the symbols indicate the distances between their latent space representations: symbols that are relatively closer to one another have more-similar latent space representations than symbols that are further apart. An insight exploited in this, and other, examples is that angiographic images that have similar latent space representations, i.e. representations with a relatively small distance between them, tend to have similar treatment procedure outcomes. This is illustrated by the upper half of the latent space in the central portion of FIG. 3 tending to have ground truth procedure outcome data 150'$_{GT}$ that represents successful outcomes, i.e. un-filled circular symbols, and the lower half of the latent space in the central portion of FIG. 3 tending to have ground truth procedure outcome data 150'$_{GT}$ that represent unsuccessful outcomes, i.e. dark-filled circular symbols. During inference, the ground truth procedure outcome data 150'$_{GT}$ of angiographic training images 130' that have latent space representations $z_t$ within a predetermined distance 160 of the latent space representation $z_i$ of the inputted angiographic image, are identified. This distance may be measured by a function such as the Euclidean distance or the geodesic distance. The success metric 110 for the inputted angiographic image is then calculated using the ground truth procedure outcome data for these identified angiographic training images 130'. The ground truth procedure outcome data 150'$_{GT}$ of the angiographic training images 130' having latent space representations within the predetermined distance 160 may be analyzed in various ways.

By way of an example, the ground truth procedure outcome data 150'$_{GT}$ may represent a binary classification of the success or failure of a treatment procedure. The success metric 110 may be calculated from ground truth procedure outcome data 150'$_{GT}$ with such a binary classification by computing a ratio of the total number of successful outcomes in the ground truth procedure outcome data 150'$_{GT}$, i.e. un-filled circular symbols, to all outcomes in the ground truth procedure outcome data 150'$_{GT}$, i.e. un-filled circular symbols and dark-filled circular symbols, that are within the predetermined distance 160 of the latent space representation $z_i$ of the inputted angiographic image. This ratio provides a probability of success, and may be used as the success metric 110. This ratio may also be converted to a binary outcome, i.e. a success or a failure of the treatment procedure by applying a threshold, such as 50 percent, to the ratio. This ratio may also be computed separately for each device type that may be used to perform the treatment. That is, for example, separately computing the ratio of the total number of successful outcomes in the ground truth procedure outcome data using a stent retriever device to all outcomes in the ground truth procedure outcome data using a stent retriever device, and the ratio of the total number of successful outcomes in the ground truth procedure outcome data using an aspiration catheter device to all outcomes in the ground truth procedure outcome data using an aspiration device, that are within the predetermined distance 160 of the latent space representation $z_i$ of the inputted angiographic image.

The success metric 110 may also be calculated in other ways, depending on the nature of the ground truth procedure outcome data 150'$_{GT}$. As mentioned above, the ground truth procedure outcome data may include one or more outcome factors. The outcome factors may include a classified outcome, such as a success or a failure of the procedure. Alternatively or additionally, the ground truth procedure outcome data may include one or more outcome factors such as a speed of the procedure, a measure of completeness of re-perfusion being achieved by the procedure, a 90-day mortality, or a 90-day modified Rankin Scale "mRS", and whether the procedure needed to be repeated. Such outcome factors may include an associated probability of their occurrence.

When a single outcome factor with binary outcome values is used to calculate the success metric 110, the success metric may be determined as described above for the binary classification of the success or failure of a treatment procedure or for the calculation of a probability of success of a treatment procedure. When a single outcome factor with a range of possible outcome values is used, such as the speed of the procedure, or the measure of completeness of re-perfusion, the outcome values may be digitized to provide binary outcome values representing positive and negative outcomes by applying a threshold to the range of possible outcome values. A percentage measure of completeness of re-perfusion may be digitized in such a manner, for example. The binary outcome values may then be used to determine a ratio of the total number of positive outcomes, to all outcomes, within the predetermined distance 160 of the latent space representation $z_i$ of the inputted angiographic image to provide a probability of success, which may be used as the success metric 110, as described above.

Alternatively, the un-digitized outcome values for ground truth procedure outcome data 150'$_{GT}$ having latent space representations $z_t$ within the predetermined distance 160 of the latent space representation $z_i$ of an inputted image may be combined in another manner. For example, these un-digitized values may be averaged to provide the success metric 110. Outcome factors such as the speed of a procedure may be averaged in this manner, for example.

When multiple outcome factors are used to calculate the success metric 110, the outcome values of angiographic training images 130' having latent space representations $z_t$ that are within a predetermined distance 160 of the latent space representation $z_i$ of the inputted angiographic image, may for example be weighted with weighting values for each outcome factor, and summed to provide the success metric 110.

In some examples, the predetermined distance 160 may be set to a predefined value. For example, if the trained neural network 140 is a VAE, then the predetermined distance 160 may be set based on the standard deviation, σ, learned by the neural network. For instance, the predetermined distance 160 may be set to 0.256 around $z_i$. In other examples, the predetermined distance 160 may be set based on user input. In one example, the method described with reference to FIG. 1 includes:

receiving user input indicative of an extent of the predetermined distance 160, and the method further comprises outputting:

a graphical representation of the latent space representation of the inputted angiographic image $z_i$;

a graphical representation of the latent space representations of at least some of the angiographic training images 130' used to train the neural network $z_j$; and an indication of the predetermined distance 160.

In this example, the user input indicative of the predetermined distance may be received via a graphical user interface "GUI", for example. The graphical representations may also be outputted to the GUI. By allowing the user to set the predetermined distance, the user may trade-off the accuracy of the neural network's predictions against the confidence of its predictions. Reducing the predetermined distance 160 has the effect of increasing the accuracy of the predictions because only the outcomes of more-similar angiographic images are considered when determining the success metric 110. However, this also reduces the total number of outcomes that are used to calculate the success metric, and thus may ultimately decrease the confidence in the neural network's predictions. The graphical representation of the latent space representations of the angiographic training images 130' may be generated using an algorithm such as t-distributed Stochastic Neighbor Embedding "t-SNE", for example. This algorithm may be used to project high-dimensional latent representations to two, or three dimensions, or to another number of dimensions, to provide an intuitive visualization of the latent space. The latent space representations of the angiographic training images that were used to train the neural network 140 may also be labelled with their ground truth procedure outcome data. The labels may for example distinguish successful outcomes from unsuccessful outcomes, as illustrated by the un-filled and dark-filled circular symbols in the central portion of FIG. 3A. The labels may also distinguish different types of treatment procedures that were used to train the neural network 140. The labels may for example include colors, or shapes that distinguish the different outcomes, and different treatment procedures. The labels may also be grouped together. For example, labels that indicate a successful outcome may be provided with a perimeter or a predefined level of transparency, in order to distinguish them from labels that indicate an unsuccessful outcome. In so doing, a user may visualize the group to which the angiographic images 130 inputted into the neural network 140 pertain.

Confidence values may also be calculated and outputted for each of the angiographic images 130 that are inputted into the neural network 140 during inference. In the example illustrated in FIG. 3B, the confidence values may be calculated using the decoder component of the VAE on the right-hand side of the neural network 140. During training, the decoder component was trained to reconstruct the inputted angiographic image 130, as described above. At inference, a difference, or error, between the inputted angiographic image 130, and the reconstructed angiographic image 130 that is generated by the decoder component, may be calculated using a function such as the structural similarity loss, the L1 norm, or the L2 norm, for example. This error provides a measure of how well the network is able to reconstruct the input at inference time, and provides a confidence value for the latent representation $z_i$. This error may be used to calculate the confidence value. Low error values indicate high confidence, and vice versa. If the confidence value is below a threshold value, a user may be notified of this, for example by means of a display. The predictions of the neural network may also be inhibited, or prevented from being outputted, if the confidence value is below the threshold value. In so doing, it is prevented that the user relies upon unreliable predictions. A low confidence value may also indicate that the neural network 140 does not generalize to the current data and may need to be retrained with additional data. As mentioned above, confidence values may alternatively be computed using the neural network by using the dropout technique.

The method described with reference to FIG. 1 may be used to calculate the success metric 110 for a plurality of different types of treatment procedures. The method may therefore be used prior to a treatment procedure commencing, i.e. in a planning stage, or immediately prior to a treatment procedure commencing, in order to select the most appropriate treatment procedure from multiple potential treatment procedures. The method may also be used during a current treatment procedure, wherein the success metric may be provided for the current treatment procedure, as well as for one or more alternative treatment procedures. In so doing, a user may be re-assured of their chosen current treatment procedure, and also informed of an alternative treatment procedure(s) that may be selected instead in the event that the physician experiences difficulties with the current treatment procedure. The success metric may be calculated for a mechanical thrombectomy procedure that includes a stent retriever device, and also for a catheter aspiration device, for example, as explained above. The values of the success metrics may therefore assist a user in selecting an optimal treatment procedure. In one example, different neural networks may be trained, each with angiographic training data for a particular type of treatment procedure, and the outputs of the different neural networks may be compared in order to determine the optimal procedure. In another example, the neural network 140 may be trained using angiographic training data from multiple different types of procedures, and the success metric 110 may be calculated for each of the multiple procedures using the ground truth procedure outcome data $150'_{GT}$ for the procedure.

In general, it is not essential that the angiographic images 130 that are inputted into the neural network 130 at inference include the treatment device that is used to perform the treatment procedure. At inference, the neural network may observe features in the inputted angiographic images 130, such as the tortuosity of the vasculature surrounding the thrombus, and uses these features to generate its output. Thus, the success metric 110 may be calculated without the need to insert a treatment device into the vasculature. However, if the device used to perform the treatment procedure is present in the angiographic images 130 that are inputted into the neural network 140 at inference, then the predictions of the neural network may be more accurate. For instance, if the position of the treatment device is known in relation to the thrombus, parameters such as the angle between a distal end of the treatment device and the thrombus, might also be encoded in the latent space representations $z_t$ of the neural network, and this might also be used to calculate the success metric 110.

In one example, the angiographic images 130 also include a deployment catheter 170 for deploying a mechanical thrombectomy device to treat the thrombus 120. In this example, the calculated success metric 110 is the success metric achieved by deploying the mechanical thrombectomy device from the deployment catheter. In this example, the mechanical thrombectomy device may be a stent retriever, or an aspiration catheter type of treatment device, for example. In this example, the angiographic training data that is used to train the neural network, also includes angiographic training images 130' that include a deployment catheter. Thus, the neural network 140 may be trained to encode the position of the deployment catheter respective the thrombus in its latent space representations $z_t$, and this may also be used to calculate the success metric 110.

In this example, the angiographic image data 130 that is inputted into the neural network at inference may include a temporal sequence of real-time angiographic images. The success metric 110 may then be provided in real-time for each angiographic image. Thus, as the deployment catheter is advanced through the vasculature towards the thrombus, the real-time success metric may be used to inform a user of the position at which the mechanical thrombectomy device may be deployed from the deployment catheter to perform the treatment procedure in order to achieve a desired level of success. Alternatively, the real-time success metric may also be used to inform a user of the type of mechanical thrombectomy device (e.g., stent retriever or aspiration catheter) that may be deployed from the deployment catheter to perform the treatment procedure in order to achieve a desired level of success.

Figure 4:
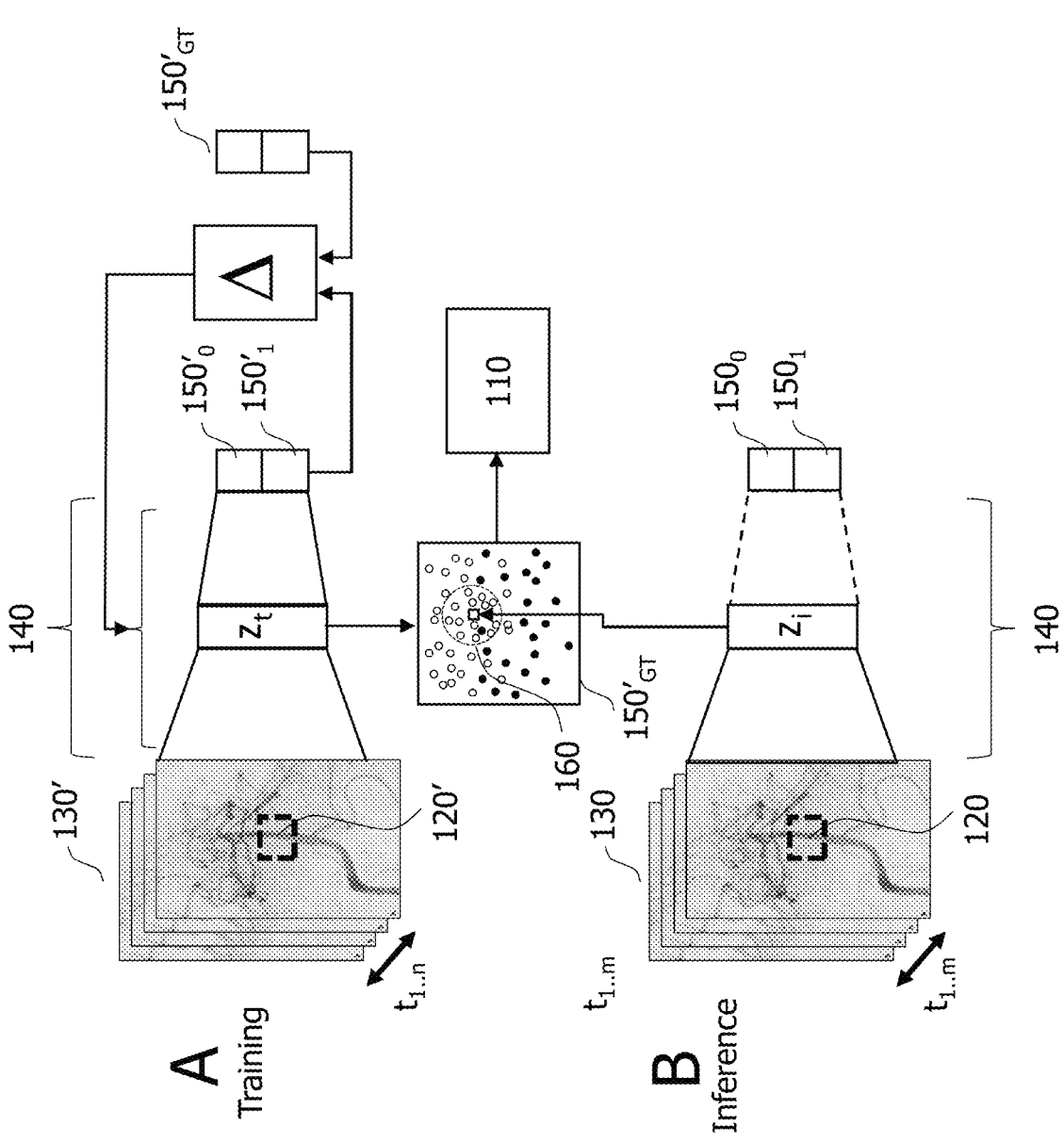
FIG. 4 is a schematic diagram illustrating A) a second example of the training of a neural network 140 to generate latent space representations $z_t$ of inputted angiographic images 130', and B) the performance of inference with the trained second example of a neural network 140, in accordance with some aspects of the present disclosure.

The neural network 140 may also be trained in a different manner to that described above with reference to FIG. 3. FIG. 4 is a schematic diagram illustrating A) a second example of the training of a neural network 140 to generate latent space representations $z_t$ of inputted angiographic images 130', and B) the performance of inference with the trained second example of a neural network 140, in accordance with some aspects of the present disclosure. The example illustrated in FIG. 4 shares with the example in FIG. 3 the principle that the neural network 140 is trained to generate latent space representations $z_i$ representing the inputted angiographic images 130. The example in FIG. 4 also shares with the example in FIG. 3 the principle that the ground truth outcome data $150'_{GT}$ of angiographic training images having similar latent space representations $z_t$ to the latent space representation $z_i$ of the inputted angiographic images, are analyzed in order to calculate the success metric 110. In contrast to the FIG. 3 example and in which the neural network was trained to reconstruct the inputted angiographic training images, in the FIG. 4 example, the neural network is trained to predict a procedure outcome $150'_{0,1}$ that will be achieved by performing the procedure on the thrombus. The neural network 140 illustrated in FIG. 4 may also have a similar architecture to that in the example in FIG. 3.

In this example, the neural network 140 is trained to generate latent space representations z representing the inputted angiographic images 130, by:

receiving angiographic training data, including a plurality of angiographic training images 130', and wherein each training image comprises a thrombus 120';

receiving ground truth procedure outcome data $150'_{GT}$ corresponding to the angiographic training data, the ground truth procedure outcome data representing, for each angiographic training image, a success or a failure achieved by performing the treatment procedure on the thrombus;

inputting the angiographic training data into the neural network; and for each of a plurality of the inputted angiographic training images:

generating a latent space representation $z_t$ of the inputted angiographic training image, using the neural network 140;

predicting a procedure outcome $150'_{0,1}$ achieved by performing the procedure on the thrombus from the latent space representation $z_t$, using the neural network 140; and adjusting parameters of the neural network 140 based on a difference between the ground truth procedure outcome $150'_{GT}$ and the predicted procedure outcome $150'_{0,1}$, for the inputted angiographic training image; and repeating the generating, the predicting, and the adjusting, until a stopping criterion is met.

Thus, in the FIG. 4 example, the neural network 140 is trained to generate latent space representations $z_t$ of inputted angiographic images 130, using the ground truth procedure outcome $150'_{GT}$ of angiographic training images. The ground truth procedure outcome $150'_{GT}$ may for example be a binary value representing a success or failure of the procedure. Alternatively, the ground truth procedure outcome $150'_{GT}$ may be a percentage chance of success or failure of the procedure. In this example, the adjusting of the parameters of the neural network 140 during training may be performed using backpropagation, as described above. The difference between the ground truth procedure outcome $150'_{GT}$ and the predicted procedure outcome $150'_{0,1}$, for the inputted angiographic training image, and which is used to adjust the parameters of the neural network 140, is illustrated in FIG. 4 by the symbol D. The value of this difference may be calculated using a loss function such as L1 norm, L2 norm, binary cross entropy, and so forth.

Inference may be performed with the neural network 140 illustrated in FIG. 4 in the same manner as described for FIG. 3. In other words, the neural network 140 is trained to generate latent space representations $z_i$ representing the inputted angiographic images 130, and at inference, the method described with reference to FIG. 1 comprises:

generating, for each inputted angiographic image, a latent space representation $z_i$, using the neural network 140; and wherein the calculating S130 the success metric 110 based on the output of the neural network 140, comprises analyzing the ground truth procedure outcome data $150'_{GT}$ of angiographic training images 130' having latent space representations $z_t$ within a predetermined distance 160 of the latent space representation $z_i$ of the inputted angiographic image, and calculating the success metric 110 for the inputted angiographic image based on the analyzed ground truth procedure outcome data.

In another example, the neural network 140 is trained to predict the procedure outcome $150'_{0,1}$ that will be achieved by performing the procedure on the thrombus, as in the FIG. 4 example. However, in contrast to the FIG. 4 example, in this example the predicted procedure outcome $150'_{0,1}$ is itself used to calculate the success metric 110 for an inputted image, rather than the success metric being calculated by analyzing the ground truth outcome data $150'_{GT}$ of angiographic training images having similar latent space representations $z_t$ to the latent space representation $z_i$ representing the inputted image. This example is described with reference to FIG. 5, which is a schematic diagram illustrating A) a third example of the training of a neural network 140 to classify inputted angiographic images 130' with an expected outcome $150_{0,1}$ of the procedure, and B) the performance of inference with the trained third example of a neural network 140, in accordance with some aspects of the present disclosure.

In this example, the neural network 140 is trained to classify the inputted angiographic images 130 with an expected outcome $150_{0,1}$ of the procedure, by:

receiving angiographic training data, including a plurality of angiographic training images 130', and wherein each training image comprises a thrombus 120;

receiving ground truth procedure outcome data $150'_{GT}$ corresponding to the angiographic training data, the ground truth procedure outcome data representing, for each angiographic training image a success or a failure achieved by performing the treatment procedure on the thrombus;

inputting the angiographic training data into the neural network 140; and for each of a plurality of the angiographic training images 130':

predicting a procedure outcome $150'_{0,1}$ achieved by performing the procedure on the thrombus, using the neural network 140; and adjusting parameters of the neural network 140 based on a difference between the predicted procedure outcome $150'_{0,1}$ and the ground truth procedure outcome data $150'_{GT}$ for the inputted angiographic training image; and repeating the predicting, and the adjusting, until a stopping criterion is met.

Figure 5:
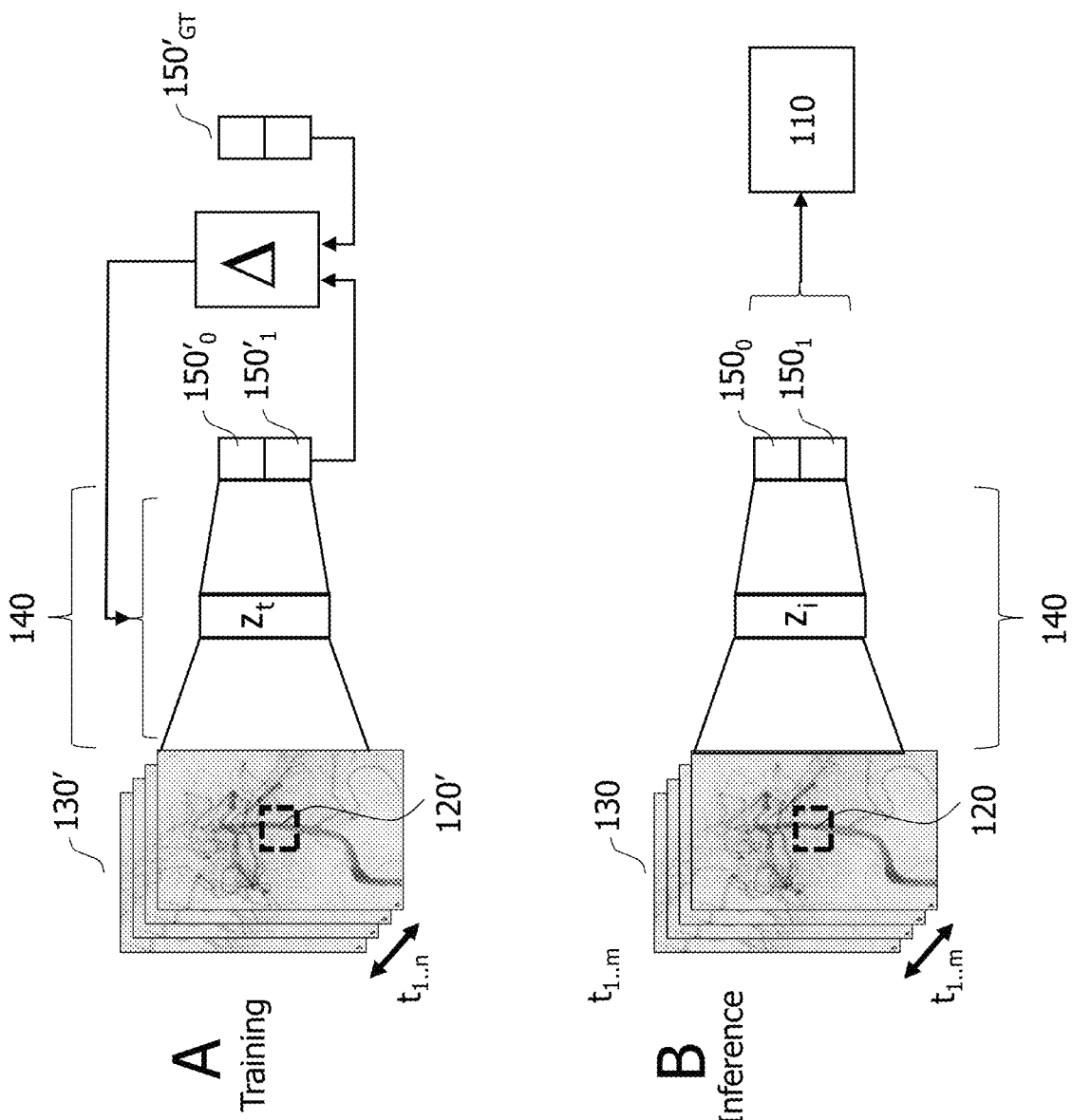
FIG. 5 is a schematic diagram illustrating A) a third example of the training of a neural network 140 to classify inputted angiographic images 130' with an expected outcome 150$_{0,1}$ of the procedure, and B) the performance of inference with the trained third example of a neural network 140, in accordance with some aspects of the present disclosure.

The neural network 140 in the example illustrated in FIG. 5 may have a similar architecture to that of the example in FIG. 3. As in the FIG. 3 example, in the FIG. 5 example, the ground truth procedure outcome $150'_{GT}$ may for example be a binary value representing a success or failure of the procedure. Alternatively, the ground truth procedure outcome $150'_{GT}$ may be a percentage chance of success or failure of the procedure. The adjusting of the parameters of the neural network 140 during training may be performed using backpropagation, as described above. The difference between the predicted procedure outcome $150'_{0,1}$ and the ground truth procedure outcome data $150'_{GT}$ for the inputted angiographic training image, and which is used to adjust the parameters of the neural network 140, is illustrated in FIG. 5 by the symbol D. The value of this difference may be calculated using a loss function such as L1 norm, L2 norm, binary cross entropy, and so forth.

In this FIG. 5 example, inference may be performed by inputting angiographic images 130 into the trained neural network 140. However, unlike the FIG. 4 example, and in which the ground truth procedure outcomes 150'$_{GT}$ of angiographic training images having similar latent space representations are analyzed to determine the success metric 110 for an inputted image, in the FIG. 5 example, the success metric 110 is predicted by the neural network 140 itself.

In this example, the neural network 140 is trained to classify the inputted angiographic images 130 with an expected outcome 150$_{0,1}$ of the procedure. At inference, the method described with reference to FIG. 1 comprises:

classifying each inputted angiographic image 130 with an expected outcome 150$_{0,1}$ of the procedure, using the neural network 140; and wherein the calculating S130 the success metric 110 based on the output of the neural network 140, comprises calculating the success metric 110 for the inputted angiographic image based on the classified expected outcome 150$_{0,1}$ of the procedure.

In this example, the success metric may be provided by the classified expected outcome 150$_{0,1}$ itself. For example, if the success metric is based on a single outcome factor, such as the success or failure of the procedure, the classified expected outcome 150$_{0,1}$ directly provides the success metric 110. However, if the success metric is based on multiple outcome factors, the classified expected outcome 150$_{0,1}$ may be calculated for each of these outcome factors, and the results may be combined, for example by weighting and summing their values, to provide the success metric 110.

In another example, the neural network 140 is trained using temporal sequences of angiographic training images 130', and each temporal sequence includes a thrombus 120' and a deployment catheter 170'. In this example, the neural network 140 is trained to perform a future prediction task. In particular, the neural network 140 is trained to predict the future position of the deployment catheter 170' in a future angiographic training image 130'. In this example, the neural network is trained to generate latent space representations $z_i$ of inputted angiographic training images, and the success metric 110 for an inputted image is determined by analyzing the ground truth procedure outcomes 150'$_{GT}$ of angiographic training images having similar latent space representations $z_t$ to that of the inputted image, as in the FIG. 3 and FIG. 4 examples. This example is described with reference to FIG. 6, which is a schematic diagram illustrating A) a fourth example of the training of a neural network 140 to generate latent space representations $z_i$ for inputted angiographic images 130' and to predict from the generated latent space representations $z_i$ future angiographic images 130$_{future}$ to the inputted angiographic images 130, and B) the performance of inference with the trained fourth example of a neural network 140, in accordance with some aspects of the present disclosure.

In this example, the neural network 140 is trained to generate latent space representations $z_i$ representing the inputted angiographic images 130 and to predict, from the generated latent space representations $z_i$, future angiographic images 130$_{future}$ to the inputted angiographic images 130, the future angiographic images including predicted future positions of the deployment catheter 170, by:

receiving angiographic training data, including a plurality of temporal sequences of angiographic training images 130', and wherein each temporal sequence of training images comprises a thrombus 120' and a deployment catheter 170';

inputting the angiographic training data into the neural network 140; and for each temporal sequence of angiographic training images 130':

generating, for each angiographic training image in the temporal sequence, a latent space representation $z_t$ of the inputted angiographic training image, using the neural network 140;

predicting, from the generated latent space representation $z_t$, a future angiographic image 130'$_{future}$ to the inputted angiographic image, the future angiographic image including a predicted future position of the deployment catheter 170;

adjusting parameters of the neural network 140 based on a difference between the predicted future angiographic image 130'$_{future}$ to the inputted angiographic image, and the corresponding future angiographic image to the inputted angiographic image 130' from the angiographic training data; and repeating the generating, the predicting, and the adjusting, until a stopping criterion is met.

Figure 6:
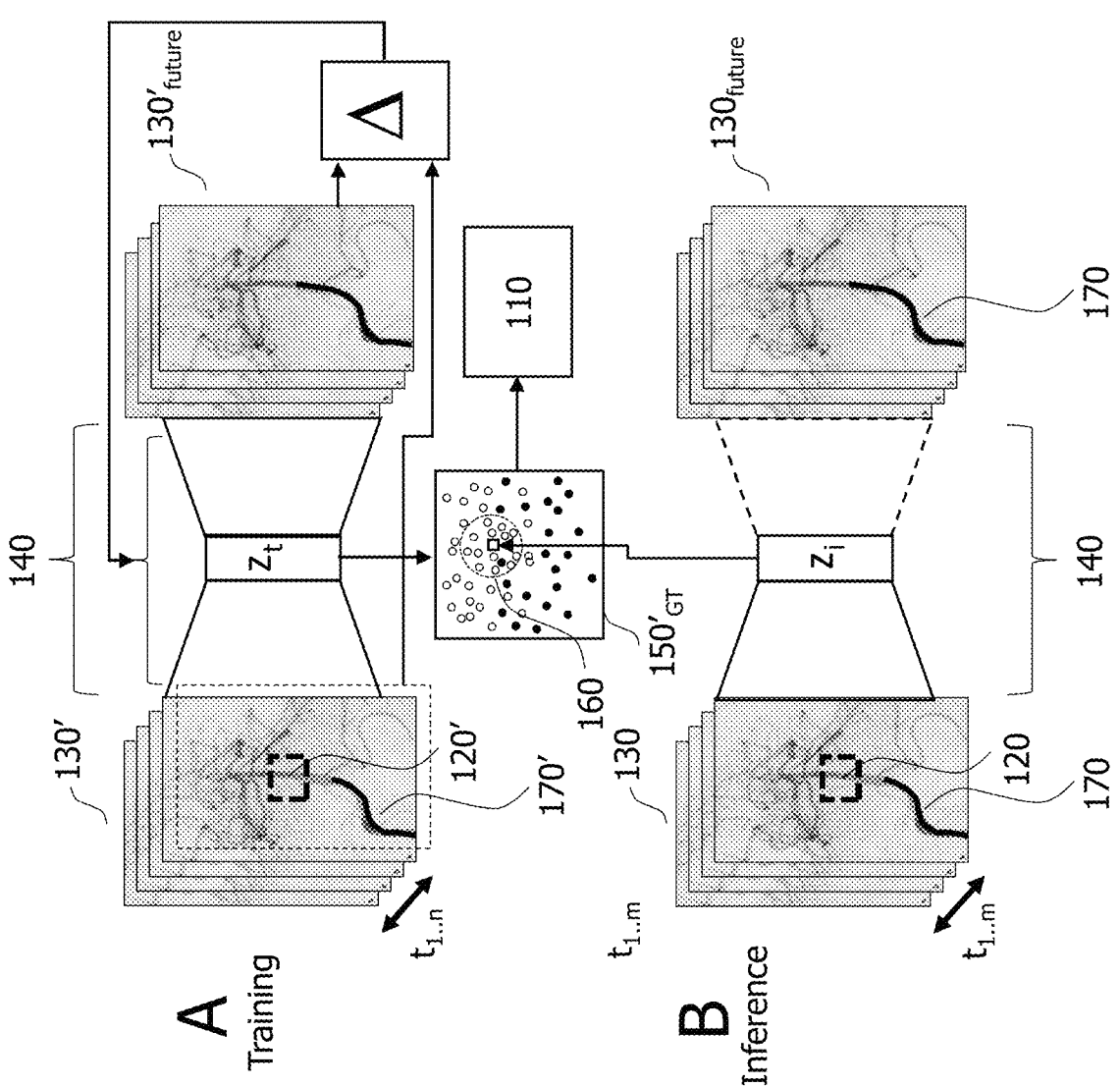
FIG. 6 is a schematic diagram illustrating A) a fourth example of the training of a neural network 140 to generate latent space representations $z_i$ for inputted angiographic images 130' and to predict from the generated latent space representations $z_i$ future angiographic images 130$_{future}$ to the inputted angiographic images 130, and B) the performance of inference with the trained fourth example of a neural network 140, in accordance with some aspects of the present disclosure.

The neural network 140 in the example illustrated in FIG. 6 may have a similar architecture to that of the example in FIG. 3. As in the FIG. 3 example, in this example, the ground truth procedure outcome 150'$_{GT}$ may for example be a binary value representing a success or failure of the procedure. Alternatively, the ground truth procedure outcome 150'$_{GT}$ may be a percentage chance of success or failure of the procedure. In this example, the angiographic training data includes a plurality of temporal sequences of angiographic training images 130'. The temporal sequences represent treatment procedures that have been performed on one or more patients. The temporal sequences include a thrombus and a deployment catheter 170'. The deployment catheter is used in the treatment procedure to deploy a treatment device such as a mechanical thrombectomy device to treat the thrombus 120 and thereby achieve the corresponding ground truth procedure outcome 150'$_{GT}$. A temporal sequence may represent the deployment catheter in multiple positions during the treatment procedure. These temporal sequences of angiographic training images 130' are used to train the neural network 140. At inference, the ground truth procedure outcome data 150'GT that corresponds to the angiographic training images 130' is analyzed in order to calculate the success metric 110. However, the ground truth procedure outcome data 150'$_{GT}$ is not required to train the neural network 140. Rather, the above operations represent a future prediction task, in which the neural network 140 is trained with the temporal sequences of angiographic training images 130' to predict a future angiographic image 130'$_{future}$ to each inputted angiographic image. By way of an example, the future angiographic image 130'$_{future}$ to the inputted angiographic image that is predicted in this example may be the next angiographic image in the temporal sequence. Alternatively, the future angiographic image 130'$_{future}$ may be a later image in the temporal sequence. The adjusting of the parameters of the neural network 140 during training may be performed using backpropagation, as described above. The difference between the predicted future angiographic image 130'$_{future}$ to the inputted angiographic image, and the corresponding future angiographic image to the inputted angiographic image 130', and which is used to adjust the parameters of the neural network 140, is illustrated in FIG. 6 by the symbol D. The value of this difference may be calculated using a loss function such as L1 norm, L2 norm, structural similarity loss, and so forth.

Inference may be performed with the neural network 140 illustrated in FIG. 6 in a similar manner as described for FIG. 3, i.e. by inputting angiographic images 130, determining their latent space representations and analyzing the ground truth procedure outcomes $150'_{GT}$ of angiographic training images having similar latent space representations $z_t$, in order to calculate the success metric 110 for an inputted image or for a predicted future image.

In this example, the received angiographic image data includes a plurality of angiographic images 130 comprising the thrombus 120, wherein the angiographic images 130 further include a deployment catheter 170 for deploying a mechanical thrombectomy device to treat the thrombus 120, and wherein the success metric is the success metric achieved by deploying the mechanical thrombectomy device from the deployment catheter; and wherein the neural network 140 is trained to generate latent space representations $z_i$ representing the inputted angiographic images 130 and to predict, from the generated latent space representations future angiographic images $130_{future}$ to the inputted angiographic images 130, the future angiographic images $130_{future}$ re including predicted future positions of the deployment catheter 170. At inference, the method described with reference to FIG. 1 comprises:

generating, for each inputted angiographic image 130, a latent space representation $z_i$, using the neural network 140; and wherein the calculating the success metric 110 based on the output of the neural network 140, comprises analyzing the ground truth procedure outcome data $150'_{GT}$ of angiographic training images 130' having latent space representations $z_t$ within a predetermined distance 160 of the latent space representation $z_i$ of the inputted angiographic image 130, and calculating the success metric 110 for a predicted future angiographic image $130_{future}$ to the inputted angiographic image 130, based on the analyzed ground truth procedure outcome data.

In contrast to the example in FIG. 3, in this FIG. 6 example, the success metric 110 is thus calculated for a predicted future angiographic image $130_{future}$ to the inputted angiographic image 130. In other words, the success metric is provided for the expected position of the deployment catheter. The expected position may also be outputted in order to guide a user in navigating the deployment catheter. For example, the predicted angiographic image $130_{future}$ illustrated in FIG. 6 may be outputted. The image may be outputted to the display 240 illustrated in FIG. 2, for example.

In another example, inference may be performed with both the trained neural network 140 in the example illustrated in FIG. 3 and the trained neural network 140 in the example illustrated in FIG. 6. That is, the trained neural network 140 in the example illustrated in FIG. 3 is used to calculate the success metric for the inputted angiographic image showing, for instance, the current position of the deployment catheter, while the trained neural network 140 in the example illustrated in FIG. 6 is used to calculate the success metric for a predicted future angiographic image $130_{future}$ to the inputted angiographic image 130, for instance, showing the expected future position of the deployment catheter. Providing both success metrics may assist a user in deciding if additional time should be spent in the deployment catheter placement or if the treatment device should be deployed. That is, if the outputted success metric for the predicted future angiographic image shows an improvement over the outputted success metric for the current inputted angiographic image below some threshold, then the user may decide to proceed with treatment device deployment rather than improving the placement of the deployment catheter.

In the above examples, the angiographic image data that is inputted into the neural network 140 at inference, and the angiographic training data that is used to train the neural network 140, was described as including either 2D angiographic images, or 3D angiographic images. However, it is also to be appreciated that both 2D and 3D angiographic images may be inputted into the neural network. Thus, in one example, the angiographic image data includes one or more 2D angiographic images, and one or more corresponding 3D angiographic images; and the training data comprises a plurality of 2D angiographic training images, and a plurality of corresponding 3D angiographic training images.

The tortuosity of the vasculature, which is known to affect the likelihood of success of treatment procedures carried out using aspiration catheters, and stent retrievers, is more evident in 3D angiographic images. Thus, inputting both 3D and 2D angiographic images into the neural network 140 in this manner serves to improve its predictions.

In another example, treatment device data is used to improve the predictions of the neural network 140. In this example, the method described with reference to FIG. 1 includes:

receiving device data for a mechanical thrombectomy device to be used in the treatment procedure; and inputting the device data into the neural network 140; and wherein the neural network 140 is trained further using device data corresponding to the angiographic training images 130';

In this example, the device data may include information such as the size of stent in a stent retriever device. At inference, this information may be used to select the ground truth procedure outcome data $150_{GT}$ such that only the ground truth procedure outcome data for treatment procedures that have the same, or a similar stent size as the current procedure, is analyzed when calculating the success metric 110.

In another example, patient data is used to improve the accuracy of the neural network's predictions. In this example, the method described with reference to FIG. 1 includes:

receiving patient data relating to the thrombus 120; and inputting the patient data into the neural network 140; and wherein the network 140 is trained further using patient data corresponding to the angiographic training images 130'.

The patient data may for example include electronic health record "EHR" data relating to a historic procedure on the vasculature, clinical findings relating to the vasculature, and so forth. For instance, an assessment of the amount of plaque in the vasculature of the current patient may be inputted into the neural network and used to calculate the success metric by analyzing only the ground truth procedure outcome data for treatment procedures that have the same, or a similar, amount of plaque.

In another example, a region of interest, such as an extent of a thrombus, or the extent of its surrounding area may be identified in the angiographic images in the training data. In this example, during training, the difference between the inputted angiographic training image and the reconstructed inputted angiographic image, is calculated by applying a higher weighting factor within the identified region of interest than outside the identified region of interest. In this example, the region of interest may be identified using a bounding box, for example. By applying this weighting factor during training, the neural network is forced to learn representations that capture meaningful information from the region of interest, such as the thrombus, and to place less emphasis on information that is more distant from the region of interest, and which may have less impact on the success metric of the treatment procedure.

In another example, the neural network 140 is also trained to predict an angle between the delivery catheter and the thrombus. The neural network may be trained to predict this angle in a supervised manner. For example, the angiographic training images may be annotated with the angle. The angle may be labelled manually by experts. This information may assist a user in performing the treatment procedure.

In another example, a computer program product, is provided. The computer program product comprises instructions, which when executed by one or more processors, cause the one or more processors to carry out a method of predicting a success metric 110 achieved by performing a treatment procedure on a thrombus 120, the method comprising:

receiving S110 angiographic image data, including one or more angiographic images 130 comprising the thrombus 120;

inputting S120 the angiographic image data into a neural network 140; and calculating S130 the success metric 110 based on the output of the neural network 140; and wherein the neural network 140 is trained using training data comprising angiographic training images 130' representing the treatment procedure, and corresponding ground truth procedure outcome data.

In another example, a system 200 for predicting a success metric 110 achieved by performing a treatment procedure on a thrombus 120, is provided. The system comprises one or more processors 210 configured to:

receive S110 angiographic image data, including one or more angiographic images 130 comprising the thrombus 120;

input S120 the angiographic image data into a neural network 140; and calculate S130 the success metric 110 based on the output of the neural network 140; and wherein the neural network 140 is trained using training data comprising angiographic training images 130' representing the treatment procedure, and corresponding ground truth procedure outcome data.

An example of the system 200 is illustrated in FIG. 2. In some examples, the system 200 may also include one or more of: an imaging system for providing the angiographic image data, such as the example projection X-ray imaging system 220 illustrated in FIG. 2; a treatment device for performing a treatment procedure on a thrombus, such as the example mechanical thrombectomy device 230 illustrated in FIG. 2; a monitor 240 for displaying the calculated success metric 110, the angiographic image data, the GUI, other outputs generated by the system 200, and so forth; a patient bed 250; and a user input device configured to receive user input (not illustrated in FIG. 1) such as a keyboard, a mouse, a touchscreen, and so forth. The system may also include a robotic device for manipulating the treatment device.

The above examples are to be understood as illustrative of the present disclosure, and not restrictive. Further examples are also contemplated. For instance, the examples described in relation to computer-implemented methods, may also be provided by the computer program product, or by the computer-readable storage medium, controller, or by the system 200, in a corresponding manner. It is to be understood that a feature described in relation to any one example may be used alone, or in combination with other described features, and may be used in combination with one or more features of another of the examples, or a combination of other examples. Furthermore, equivalents and modifications not described above may also be employed without departing from the scope of the invention, which is defined in the accompanying claims. In the claims, the word "comprising" does not exclude other elements or operations, and the indefinite article "a" or "an" does not exclude a plurality. The mere fact that certain features are recited in mutually different dependent claims does not indicate that a combination of these features cannot be used to advantage. Any reference signs in the claims should not be construed as limiting their scope.

The invention claimed is:

1. A system for predicting a success metric for a treatment procedure performable on a thrombus, the system comprising:

a deployment catheter configured to be positioned relative to the thrombus;

an imaging system configured to generate current angiographic image data including one or more angiographic images comprising the thrombus, while the deployment catheter is positioned relative to the thrombus;

a display configured to output the success metric for the treatment procedure; and a controller configured to:

receive, from the imaging system, the current angiographic image data that includes an angiographic image comprising the thrombus;

input the angiographic image into a model configured to output a prediction, related to performance of the treatment procedure, based on the angiographic image, wherein the model is trained to determine the prediction based on a position of a deployment catheter relative to the thrombus in the angiographic image;

calculate the success metric for the treatment procedure based on the output of the model; and output, via the display, the success metric for the treatment procedure.

2. The system according to claim 1, wherein the model comprises a neural network.

3. The system according to claim 1, wherein the controller is further configured to:

train the model, to output the prediction related to the treatment procedure, based on training data comprising angiographic training images representing the treatment procedure and corresponding ground truth outcome data of the represented treatment procedure.

4. The system according to claim 3, wherein the controller is further configured to:

receive latent space representations for the angiographic training images;

generate, for the inputted angiographic image, a latent space representation based on the model;

analyze ground truth output data corresponding to each of the angiographic training images having latent space representations within a predetermined distance of the latent space representation of the inputted angiographic image; and calculate the success metric for the treatment procedure based on the analyzed ground truth outcome data.

5. The system according to claim 1, wherein the controller is further configured to:

classify the inputted angiographic image with an expected
outcome of the treatment procedure based on the
model; and calculate the success metric for the treatment procedure
based on the classified expected outcome of the treat-
ment procedure.

6. The system according to claim 1, wherein the success
metric is a metric of success for deploying the mechanical
thrombectomy device from the deployment catheter to per-
form the treatment procedure.

7. The system according to claim 1, wherein:

the received angiographic image data includes a plurality
of angiographic images including the thrombus and the
deployment catheter for deploying a mechanical throm-
bectomy device to treat the thrombus, the success metric is a success metric for deploying the
mechanical thrombectomy device from the deployment
catheter during the treatment procedure, and the controller is configured to:

input the plurality of angiographic images into the
model;

generate, based on the model, latent space representa-
tions representing the inputted plurality of angio-
graphic images; and predict, from the generated latent space representa-
tions, future angiographic images including pre-
dicted future positions of the deployment catheter.

8. The system according to claim 3, wherein the controller
is further configured to:

train the model further based on at least one of: training
device data corresponding to the angiographic training
images or training patient data corresponding to the
angiographic training images;

receive at least one of device data for a mechanical
thrombectomy device to be used in the treatment pro-
cedure and patient data relating to the thrombus; and input at least one of the device data or the patient data into
the model to output the prediction related to the per-
formance of the treatment procedure.

9. The system according to claim 1, wherein the controller
is further configured to:

calculate a confidence value for the inputted angiographic
image; and output the confidence value.

10. The system according to claim 4, wherein the con-
troller is further configured to:

receive user input indicative of an extent of the predeter-
mined distance; and output at least one of:

a graphical representation of the latent space represen-
tation of the inputted angiographic image, a graphical representation of the latent space represen-
tations of at least one of the angiographic training
images, and an indication of the predetermined distance.

11. The system according to claim 3, wherein at least one
of:

the success metric represents a probability of success of
the treatment procedure, the ground truth procedure outcome data represents a
binary classification of success or failure of the treat-
ment procedure, and the ground truth procedure outcome data comprises one or
more of: a speed of the treatment procedure, a measure
of completeness of re-perfusion achieved by the treatment procedure, a mortality rate subsequent to the
treatment procedure, and whether the treatment proce-
dure needed to be repeated.

12. The system according to claim 3, wherein the con-
troller is further configured to:

receive angiographic training data including a plurality of
angiographic training images that each include a throm-
bus;

input the angiographic training images into the model;
and for each inputted angiographic training image:

generate a latent space representation of the inputted
angiographic training image based on the model;

reconstruct the inputted angiographic training image
from the latent space representation based on the
model; and adjust parameters of the model based on a difference
between the inputted angiographic training image
and the reconstructed inputted angiographic training
image.

13. The system according to claim 3, wherein the con-
troller is further configured to:

receive the angiographic training data including a plural-
ity of angiographic training images that each comprise
a thrombus;

receive the ground truth procedure outcome data corre-
sponding to the angiographic training data, wherein, for
each angiographic training image, the ground truth
procedure outcome data represents a success or a
failure achieved when performing an instance of the
treatment procedure corresponding to the angiographic
training image;

input the angiographic training images into the model;
and for each inputted angiographic training image:

predict a procedure outcome for performance of the
treatment procedure based on the model; and adjust parameters of the model based on a difference
between the predicted procedure outcome and the
ground truth procedure outcome data for the inputted
angiographic training image.

14. The system according to claim 4, wherein the con-
troller is further configured to:

receive angiographic training data including a temporal
sequences of angiographic training images, each tem-
poral sequence of training images comprising the
thrombus and the deployment catheter;

input the angiographic training images into the model;
and for each inputted angiographic training image of the
temporal sequence:

generate a latent space representation of the inputted
angiographic training image based on the model;

predict, from the generated latent space representation,
a future angiographic image with respect to the
inputted angiographic image, the future angio-
graphic image including a predicted future position
of the deployment catheter; and adjust parameters of the model based on a difference
between the predicted future angiographic image to
the inputted angiographic image, and a future angio-
graphic image corresponding to the predicted future
angiographic image to the inputted training angio-
graphic image.

* * * * *